US012564354B2

(12) United States Patent
Itaka

(10) Patent No.: US 12,564,354 B2
(45) Date of Patent: Mar. 3, 2026

(54) CARTILAGE DEGENERATION ANALYSIS DEVICE, DEVICE FOR DIAGNOSING OR AIDING DIAGNOSIS WHICH CONTAINS SAME, METHOD FOR DETERMINING DEGREE OF DEGENERATION OF CARTILAGE, AND METHOD FOR EVALUATING DRUG EFFICACY OF TEST SUBSTANCE

(71) Applicant: Institute of Science Tokyo, Tokyo (JP)

(72) Inventor: Keiji Itaka, Tokyo (JP)

(73) Assignee: INSTITUTE OF SCIENCE TOKYO, Tokyo (JP)

( * ) Notice: Subject to any disclaimer, the term of this patent is extended or adjusted under 35 U.S.C. 154(b) by 0 days.

(21) Appl. No.: 18/264,568

(22) PCT Filed: Feb. 4, 2022

(86) PCT No.: PCT/JP2022/004512
§ 371 (c)(1),
(2) Date: Aug. 7, 2023

(87) PCT Pub. No.: WO2022/168953
PCT Pub. Date: Aug. 11, 2022

(65) Prior Publication Data
US 2024/0041392 A1 Feb. 8, 2024

(30) Foreign Application Priority Data
Feb. 8, 2021 (JP) .................................. 2021-018138

(51) Int. Cl.
*A61B 5/00* (2006.01)
(52) U.S. Cl.
CPC .......... *A61B 5/4514* (2013.01); *A61B 5/0075* (2013.01); *A61B 5/4848* (2013.01)

(58) Field of Classification Search
CPC .... A61B 5/4514; A61B 5/0075; A61B 5/4848
See application file for complete search history.

(56) References Cited

U.S. PATENT DOCUMENTS

2010/0234740 A1 9/2010 Roessler et al.
2019/0343394 A1* 11/2019 Sato ..................... A61B 5/0075
2023/0341330 A1* 10/2023 Bergholt ............ G01N 33/4833

FOREIGN PATENT DOCUMENTS

WO 2018134980 A1 7/2018

OTHER PUBLICATIONS

Pavlou et al., Raman spectroscopy for the assessment of osteoarthritis; Annals of Join; vol. 3 (Oct. 2018); published on Oct. 16, 2018 (Year: 2018).*

(Continued)

*Primary Examiner* — Chao Sheng
(74) *Attorney, Agent, or Firm* — Kilpatrick Townsend & Stockton LLP

(57) ABSTRACT

There is provided an analyzer which detects an initial stage of cartilage degeneration due to a disease such as osteoarthritis. One aspect of the present invention relates to a cartilage degeneration analyzer having a processor which includes an index calculator configured to calculate on the basis of a Raman spectrum obtained by Raman spectrometry in which excitation light is irradiated to cartilage of a subject, a value representing at least one index from a group consisting of
    Index (a): secondary structure of collagen,
    Index (b): hydration level of collagen,
    Index (c): composition and total amount of glycosaminoglycan, and
    Index (d): level of glycosylation of protein and total amount of glycosaminoglycan.

10 Claims, 9 Drawing Sheets

(56)                References Cited

OTHER PUBLICATIONS

Barrett et al.; Laser Raman inelastic light scattering investigations of hyaluronic acid primary and secondary structure; Journal of Raman Spectroscopy; vol. 8, No. 1; p. 35-38; published in Feb. 1979 (Year: 1979).*
Leikin et al.; Raman spectral evidence for hydration forces between collagen triplehelices; Biophysics and Computational Biology; vol. 94 No.21; p. 11312-11317; published on Oct. 14, 1997 (Year: 1997).*
Bergholt et al., "Raman Spectroscopy: Guiding Light for the Extracellular Matrix", Frontiers in Bioengineering and Biotechnology, vol. 7, No. 303, Nov. 1, 2019, pp. 1-16.
Dingari et al., "Raman Spectroscopy Provides a Powerful Diagnostic Tool for Accurate Determination of Albumin Glycation", PLoS One, vol. 7, No. 2, Feb. 29, 2012, pp. 1-11.
Martinez et al., "Characterisation of Structural Changes in Collagen with Raman Spectroscopy", Applied Spectroscopy Reviews, vol. 54, Jan. 9, 2019, pp. 509-542.

Nieuwoudt et al., "Raman Spectroscopy Reveals Age- and Sex-Related Differences in Cortical Bone from People with Osteoarthritis", Scientific Reports, vol. 10, No. 19443, Nov. 10, 2020, 14 pages.
Pavlou et al., "Raman Spectroscopy for the Assessment of Osteoarthritis", Annals of Joint, vol. 3, No. 83, Oct. 16, 2018, pp. 1-10.
Application No. PCT/JP2022/004512 , International Search Report and Written Opinion, Mailed On Apr. 26, 2022, 13 pages.
Takahashi et al., "Do Formalin Fixation and Freeze-Thaw Affect Near-Infrared Raman Spectroscopy of Cartilaginous Tissue? A Preliminary Ex Vivo Analysis of Native Human Articular Cartilage", Journal of Raman Spectroscopy, vol. 46, No. 11, Jun. 26, 2015, pp. 1166-1172.
Takahashi et al., "Raman Spectroscopy Investigation of Load-Assisted Microstructural Alterations in Human Knee Cartilage: Preliminary Study into Diagnostic Potential for Osteoarthritis", Journal of the Mechanical Behavior of Biomedical Materials, vol. 31, Mar. 2014, pp. 77-85.

* cited by examiner

1

CARTILAGE DEGENERATION ANALYSIS DEVICE, DEVICE FOR DIAGNOSING OR AIDING DIAGNOSIS WHICH CONTAINS SAME, METHOD FOR DETERMINING DEGREE OF DEGENERATION OF CARTILAGE, AND METHOD FOR EVALUATING DRUG EFFICACY OF TEST SUBSTANCE

TECHNICAL FIELD

The present invention relates to a cartilage degeneration analyzer, an apparatus for diagnosis or for aiding diagnosis including the same, a method for determining a degree of cartilage degeneration, and a method for evaluating a drug action of a test substance.

BACKGROUND ART

Articular cartilage, generally, has a characteristic collagen orientation structure in a thickness range of approximately 2 mm to 7 mm, and plays an important role in load distribution and lubrication of joints. Main constituents of cartilage are collagen, a glycosaminoglycan (GAG) such as chondroitin sulfate and hyaluronic acid, and water.

Diagnosis of a cartilage of a patient suffering from a disease such as osteoarthritis (OA) has hitherto been carried out by an X-ray Photograph (X-P) and nuclear magnetic resonance imaging (MRI) of a joint. However, at a stage at which subchondral bone sclerosis is observed in the X-ray of a joint, the degeneration of cartilage is already progressed substantially. On the other hand, while properties such as resilience and lubricity of cartilage change even before the observation in the X-ray, and have a close relationship with symptoms and prognosis, methods for detection and diagnosis thereof have not been investigated adequately.

As research related to degeneration of cartilage, a method of evaluating a state of a cartilaginous tissue by Raman spectrometry has been known. For instance, in Non-Patent Document 1, observations by Raman spectroscopy of a cartilage with substantially progressed degeneration of a surgical specimen have been described. Moreover, in a document such as Non-Patent Document 2, observations by Raman spectroscopy of a cartilage specimen of a healthy animal and an animal having a disease have been described.

CITATION LIST

Non-Patent Documents

Non-Patent Document 1: Takahashi, Y. et al. Raman spectroscopy investigation of load-assisted microstructural alterations in human knee cartilage: Preliminary study into diagnostic potential for osteoarthritis. J Mech Behav Biomed Mater 31: 77-85, 2014

Non-Patent Document 2: Takahashi Y. et al. Do formalin fixation and freeze-thaw affect near-infrared Raman spectroscopy of cartilaginous tissue? A preliminary ex vivo analysis of native human articular cartilage. J. Raman Spectrosc. 46: 1166-1172, 2015

SUMMARY OF THE INVENTION

Problems to be Solved by the Invention

However, in Non-Patent Documents 1 and 2, detailed investigation of an induction of biotransformation of a cartilage due to a disease such as osteoarthritis, particularly in an early stage, was not carried out. According to an aspect of the present invention, the present invention has been made in view of the abovementioned circumstances with an object of providing an analyzer which detects the initial stage of cartilage degeneration due to a disease such as osteoarthritis.

Means for Solving the Problems

The present invention and the preferred illustrative aspects of the present invention are as follow.

1. A cartilage degeneration analyzer comprising:
   a processor which includes an index calculator configured to calculate, on the basis of a Raman spectrum obtained by Raman spectrometry in which excitation light is irradiated to cartilage of a subject, a value representing at least one index from a group consisting of
   Index (a): secondary structure of collagen,
   Index (b): hydration level of collagen,
   Index (c): composition and total amount of glycosaminoglycan, and
   Index (d): level of glycosylation of protein and total amount of glycosaminoglycan.
2. The analyzer according to embodiment 1, wherein the processor further includes a judging section which is configured to determine a degree of cartilage degeneration on the basis of the value calculated by the index calculator.
3. The analyzer according to one of embodiments 1 and 2, wherein the index calculator calculates at least a value representing Index (a), and Index (a) is an abundance ratio of a random-coil collagen and an $\alpha$-helix collagen.
4. The analyzer according to any one of embodiments 1 to 3, wherein the index calculator calculates at least a value representing Index (c), and the composition of glycosaminoglycan is a quantitative ratio of chondroitin sulfate and hyaluronic acid.
5. The analyzer according to any one of embodiments 1 to 4, wherein Index (a) and Index (b) are calculated on the basis of a Raman spectrum in a region of wavenumbers from $1170$ $cm^{-1}$ to $1500$ $cm^{-1}$.
6. The analyzer according to any one of embodiments 1 to 5, wherein Index (c) and Index (d) are calculated on the basis of a Raman spectrum in a region of wavenumbers from $1000$ $cm^{-1}$ to $1200$ $cm^{-1}$.
7. The analyzer according to any one of embodiments 1 to 6, wherein the value representing Index (a) is a ratio $(I_{1240}/I_{1270})$ of an integrated intensity $(I_{1240})$ of a peak of a range from $1235$ $cm^{-1}$ to $1245$ $cm^{-1}$, and an integrated intensity $(I_{1270})$ of a peak of a range from $1265$ $cm^{-1}$ to $1275$ $cm^{-1}$.
8. The analyzer according to any one of embodiments 1 to 7, wherein a value representing Index (b) is a ratio $((I_{1312+1340})/I_{1270})$ of a sum of an integrated intensity $(I_{1312})$ of a peak of a range from $1307$ $cm^{-1}$ to $1317$ $cm^{-1}$ and an integrated intensity $(I_{1340})$ of a peak of a range from $1335$ $cm^{-1}$ to $1345$ $cm^{-1}$, and the integrated intensity $(I_{1270})$ of the peak of the range from $1265$ $cm^{-1}$ to $1275$ $cm^{-1}$.
9. The analyzer according to any one of embodiments 1 to 8, wherein in Index (c), a value representing the composition of glycosaminoglycan is a ratio $(I_{1065}/I_{1123})$ of an integrated intensity $(I_{1065})$ of a peak of a range from $1060$ $cm^{-1}$ to $1070$ $cm^{-1}$ and an integrated intensity $(I_{1123})$ of a peak of a range from $1118$ $cm^{-1}$ to $1128$ $\text{cm}^{-1}$, and a value representing the total amount of glycosaminoglycan is a sum total of an integrated intensity of the peak of the range of wavenumbers from 1000 $\text{cm}^{-1}$ to 1200 $\text{cm}^{-1}$.

10. The analyzer according to any one of embodiments 1 to 9, wherein in Index (d), a value representing the level of glycosylation of protein is a ratio ($I_{1165}/I_{850}$) of an integrated intensity ($I_{1165}$) of a peak of a range from 1160 $\text{cm}^{-1}$ to 1170 $\text{cm}^{-1}$ and an integrated intensity ($I_{850}$) of a peak of a range from 845 $\text{cm}^{-1}$ to 855 $\text{cm}^{-1}$, and the value representing the total amount of glycosaminoglycan is the sum total of the integrated intensity of the peak of the range of wavenumbers from 1000 $\text{cm}^{-1}$ to 1200 $\text{cm}^{-1}$.

11. The analyzer according to any one of embodiments 1 to 10, wherein the analyzer is used for diagnosis of osteoarthritis.

12. An apparatus for diagnosis or for aiding diagnosis of osteoarthritis comprising: the analyzer according to any of embodiments 1 to 11.

13. A method for determining a degree of cartilage degeneration comprising:

calculating on the basis of a Raman spectrum obtained by Raman spectrometry in which excitation light is irradiated to cartilage of a subject, a value representing at least one index from a group consisting of Index (a): secondary structure of collagen, Index (b): hydration level of collagen, Index (c): composition and total amount of glycosaminoglycan, and Index (d): level of glycosylation of protein and total amount of glycosaminoglycan; and determining a degree of cartilage degeneration on the basis of the value calculated.

14. A method for evaluating a drug action of a test substance, comprising:

calculating on the basis of a Raman spectrum from cartilage obtained by irradiating a part of cartilage of a subjected administered with the test substance with excitation light, a value representing at least one index from a group consisting of index (a): secondary structure of collagen.

Index (b): hydration level of collagen,

Index (c): composition and total amount of glycosaminoglycan, and

Index (d): level of glycosylation of protein and total amount of glycosaminoglycan: and evaluating the drug action of the test substance on the basis of the value calculated.

15. A method for determining a degree of regeneration of cartilage comprising:

calculating on the basis of a Raman spectrum from cartilage obtained by irradiating a part of cartilage of a subject administered with the test substance with excitation light, a value representing at least one index from a group consisting of Index (a): secondary structure of collagen, Index (b): hydration level of collagen, Index (c): composition and total amount of glycosaminoglycan, and Index (d): level of glycosylation of protein and total amount of glycosaminoglycan; and determining the degree of regeneration of cartilage on the basis of the value calculated.

Effect of the Invention

According to an aspect of the present invention, it is possible to provide an analyzer which detects a degree of degeneration of cartilage, and particularly an initial stage of cartilage degeneration caused by a joint instability. Moreover, according to another aspect of the present invention, it is possible to determine a degree of degeneration in the initial stage of the degeneration of cartilage. Furthermore, according to still another aspect of the present invention, it is possible to provide an apparatus and a method for determining a degree of regeneration of cartilage by treatment. According to an aspect of the present invention it is possible to provide a method for evaluating a drug action of a test substance when the test substance is administered to a subject having a degenerated cartilage.

MODE FOR CARRYING OUT THE INVENTION

<Analyzer>

Figure 1:
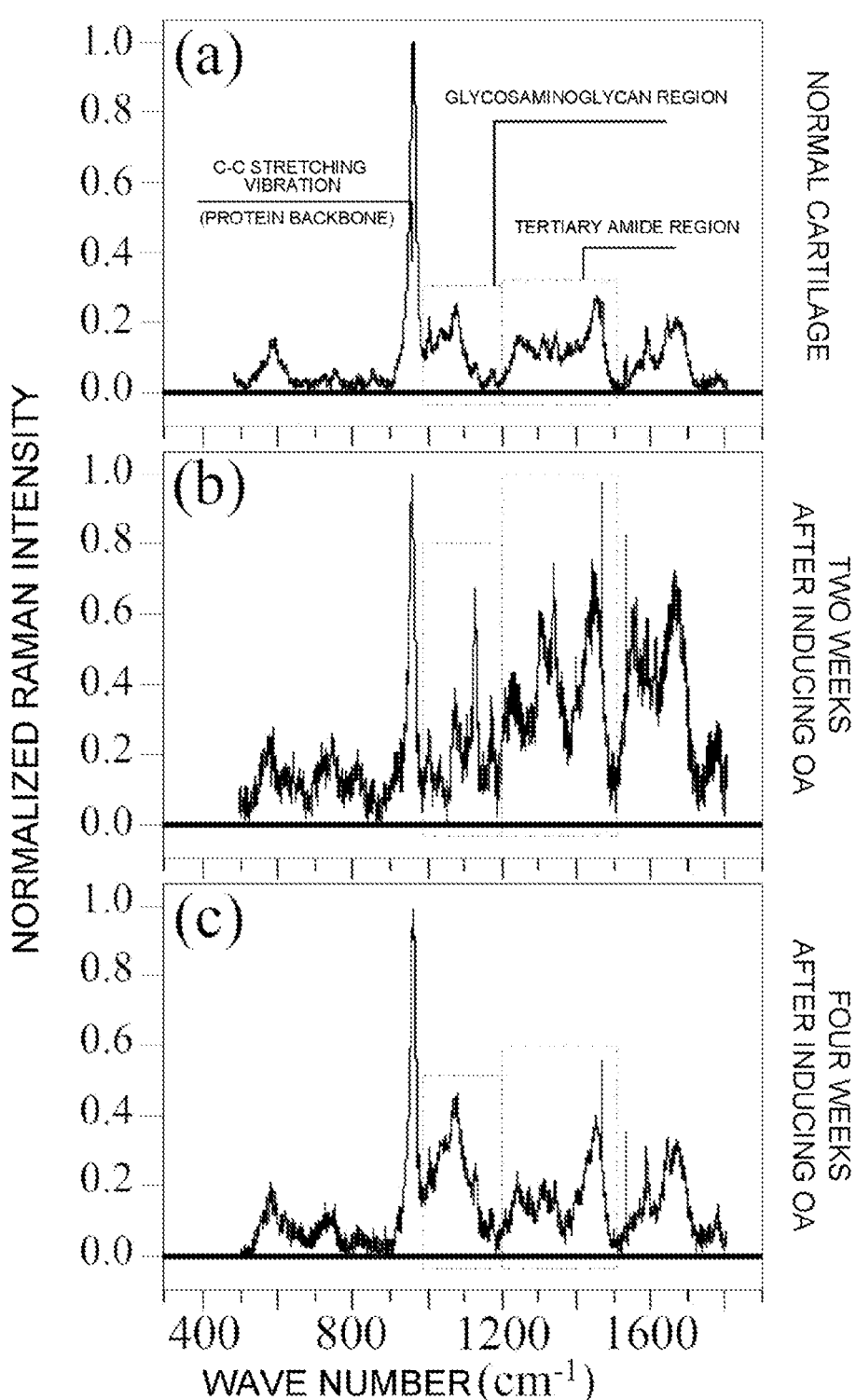
FIG. 1a is a diagram showing a Raman spectrum of a normal cartilage.
FIG. 1b is a diagram showing a Raman spectrum of a cartilage two weeks after a surgery (OA surgery) to induce joint instability.
FIG. 1c is a diagram showing a Raman spectrum of a cartilage four weeks after the OA (osteoarthritis) surgery.

An aspect of the present embodiment relates to a cartilage degeneration analyzer (also simply referred to as 'analyzer'), comprising a processor which includes an index calculator configured to calculate, on the basis of a Raman spectrum obtained by Raman spectrometry in which excitation light is irradiated to cartilage of a subject, a value representing at least one index from a group consisting of Index (a): secondary structure of collagen, Index (b): hydration level of collagen, Index (c): composition and total amount of glycosaminoglycan (also referred to as 'GAG'), and Index (d): level of glycosylation of protein and total amount of glycosaminoglycan.

Another aspect of the present embodiment relates to the analyzer, wherein the processor further includes a judging unit which is configured to determine a degree of cartilage degeneration on the basis of the value calculated by the index calculator. In the present specification, the analyzer which has the judging section is also referred to as a 'judging unit'.

As it will be described later in examples, inventors of the present invention, after having induced joint instability by removing a medial collateral ligament (MCL) and a medial meniscus (MM) of a knee joint of a mouse, performed a surgery (hereinafter, also referred to as 'OA surgery') to cause osteoarthritis, and carried out analysis of an initial stage of cartilage degeneration. Excitation light was irradiated to cartilage of the mouse subjected to the OA surgery and Raman spectrometry was carried out, and when analysis was carried out by fingerprint method, Indices (a) to (d) which enable to detect a change in the initial stage of osteoarthritis were found out. The initial stage of cartilage degeneration due to the OA surgery could not be detected by a method such as X-ray photograph or MRI, and the Indices (a) to (d) in the present embodiment are particularly effective in detection of the initial stage of cartilage degeneration (especially cartilage degeneration due to joint instability).

Moreover, the inventors of the present invention, by using the Indices (a) to (d), confirmed that by administering mRNA subjected to Runx1 encoding (also referred to as 'mRNA/Runx1') which is known as a drug for treatment of osteoarthritis to a degenerated cartilage of a mouse four weeks after the OA surgery, a molecular structure of the cartilage is recovered and regenerated.

The analyzer of the present embodiment has the processor which includes the index calculator which is configured to calculate a value representing at least one index from the group consisting of Indices (a) to (d) on the basis of a Raman spectrum obtained by Raman spectrometry in which excitation light is irradiated to cartilage of a subject. In the present specification, the 'subject' signifies an animal which may become a subject to be judged, and a mammal such as a human, a mouse, a rat, a hamster, a guinea pig, a monkey, a cow, a pig, a horse, a rabbit, a sheep, a goat, a cat, and a dog is preferable. As the excitation light to be used for Raman spectrometry, light such as laser light is preferable, and semiconductor laser (laser diode) is more preferable. A wavelength of excitation light in a range of 244 nm to 1064 nm is preferable, and a wavelength in a range of 400 nm to 800 nm is more preferable. A part on which the excitation light is to be irradiated may be a cartilage of a joint having a disorder or may be a cartilage of a healthy joint.

In the present embodiment, Index (a) and Index (b) are indices based on a Raman spectrum in a tertiary amide region, and Index (c) and Index (d) are indices based on a Raman spectrum of a glycosaminoglycan region. This is described below in detail.

<Index in Tertiary Amide Region>

A Raman band derived from collagen in a cartilage is observed in the tertiary amide region. Tertiary amide region means a region of wavenumbers in a range from $1170 \text{ cm}^{-1}$ to $1500 \text{ cm}^{-1}$. The inventors of the present invention compared results of Raman spectrometry for a normal cartilage and a cartilage in an initial stage of degeneration, and found out 'Index (a): secondary structure of collagen' and 'Index (b): hydration level of collagen' for determining the degree of cartilage degeneration in the tertiary amide region. When Index (a) and Index (b) are combined, it is possible to determine in more detail, the degree of degeneration of cartilage based on the change in collagen.

<Index (a)>

Index (a) is a secondary structure of collagen in cartilage. As it will be described later in examples, it is presumed that the secondary structure of collagen changes in two stages with the progression of cartilage degeneration. In FIG. 6c, a change in the secondary structure of collagen in cartilage with degeneration of cartilage is shown schematically. Collagen of a normal cartilage (also referred to as 'healthy cartilage') has an α-helix structure having a hydrogen bond inside the structure, and form a helical structure. However, as the degeneration of cartilage progresses, the hydrogen bond inside the α-helix structure recedes gradually and the helical structure is loosened, and by forming a hydrogen bond with an external water molecule, a more open α-helix structure is formed. The α-helix structure and the open α-helix structure which is loosened are presumed to change reversibly. However, as the cartilage degeneration progresses further, the α-helix structure is disintegrated irreversibly, and a random-coil structure is formed.

Such secondary structure of collagen protein of a cartilage is reflected is the Raman spectrum of the tertiary amide region. A Raman band derived from the random-coil structure has an intensity peak near wavenumber $1240 \text{ cm}^{-1}$, and preferably in a range from $1235 \text{ cm}^{-1}$ to $1245 \text{ cm}^{-1}$. Whereas, a Raman band derived from the α-helix collagen has an intensity peak near wavenumber $1270 \text{ cm}^{-1}$, and preferably in a range from $1265 \text{ cm}^{-1}$ to $1275 \text{ cm}^{-1}$. In the present specification, the intensity of the Raman band near the wavenumber $1240 \text{ cm}^{-1}$ and the intensity of the Raman band near the wavenumber $1270 \text{ cm}^{-1}$ are denoted as $I_{1240}$ and $I_{1270}$ respectively (hereinafter, for Raman bands near the other wavenumbers are also denoted similarly). In the present specification, the intensity of a Raman band signifies an integrated intensity.

A preferable aspect of Index (a) is an abundance ratio of the random-coil collagen and the α-helix collagen in cartilage. The value representing Index (a), for instance, can be expressed by a ratio of the intensity of the Raman band derived from the random-coil collagen and the intensity of the Raman band derived from the α-helix collagen. It is preferable that the value representing Index (a) is, for example, a ratio ($I_{1240}/I_{1270}$) of an integrated intensity ($I_{1240}$) of a peak of a range from 1235 cm$^{-1}$ to 1245 cm$^{-1}$ and an integrated intensity ($I_{1270}$) of a peak of a range from 1265 cm$^{-1}$ to 1275 cm$^{-1}$. The value of ($I_{1240}/I_{1270}$) becomes larger with the progression of osteoarthritis. Although it is not restricted in particular, when the value of $I_{1240}/I_{1270}$ of cartilage of a subject is 1.3 times or more than 1.3 times the value for a normal cartilage (reference value) for example, a judgment is to be made that osteoarthritis has progressed.
<Index (b)>

Index (b) is a hydration level of collagen. As mentioned above, as the degeneration of cartilage progresses, the hydrogen bond inside the α-helix structure recedes gradually, and is loosened, and the external water molecule and each of a N—H group and a C═O group of an amide of collagen form a hydrogen bond.

A preferable aspect of Index (b) is a proportion of amide hydrated in the α-helix collagen. The value representing Index (b), for instance, can be expressed by a ratio of an intensity of a band derived from the amide hydrated in α-helix collagen and an intensity of a band derived from the α-helix collagen. The band derived from the hydrated α-helix collagen is observed near wavenumber 1312 cm$^{-1}$ and near wavenumber 1340 cm$^1$. It is preferable that the value representing Index (b) is, for example, a ratio (($I_{1312+1340}$)/$I_{1270}$) of a sum ($I_{1312+1340}$) of an integrated intensity ($I_{1312}$) of a peak of wavenumbers in a range from 1307 cm$^{-1}$ to 1317 cm$^{-1}$ and an integrated intensity ($I_{1340}$) of a peak of wavenumbers in a range from 1335 cm$^{-1}$ to 1345 cm$^{-1}$, and the integrated intensity ($I_{1270}$) of the peak of wavenumbers in the range from 1265 cm$^{-1}$ to 1275 cm$^{-1}$. With the progression of osteoarthritis, the value (($I_{1312+1340}$)/$I_{1270}$) changes in two stages reflecting a change in the secondary structure of collagen. In a first stage, the value of ($I_{1312}+I_{1340}$)/$I_{1270}$ tends to become large due to the formation of the open α-helix structure by hydrogen bonding with the external water molecule after gradual receding of the hydrogen bond inside the α-helix structure, but in a second stage, the water molecule returns to a movable state due to an increase in a proportion of the random-coil structure, as the open α-helix structure is disintegrated irreversibly, and the value of ($I_{1312+1340}$)/$I_{1270}$ decreases.

Although it is not restricted in particular, when the value of ($I_{1312+1340}$)/$I_{1270}$ is twice or more than twice the value for a normal cartilage (reference value) for example, a judgment is to be made that a degeneration of the first stage has progressed. Moreover, when the value of $I_{1240}/I_{1270}$ of Index (a) is 1.3 times or more than 1.3 times the value for the normal cartilage (reference value) for example, and the value of ($I_{1312+1340}$)/$I_{1270}$ of Index (b) is between 1.3 times to twice the value for the normal cartilage (reference value), a judgement is to be made that osteoarthritis has progressed.
<Index in Glycosaminoglycan Region>

A cartilage includes a glycosaminoglycan (also referred to as 'GAG') such as chondroitin sulfate, hyaluronic acid, heparan sulfate, and keratan sulfate, as a main constituent of an extracellular matrix. A Raman band derived from a glycosaminoglycan is observed in a glycosaminoglycan region (also referred to as 'GAG region') of wavenumbers from 1000 cm$^{-1}$ to 1200 cm$^1$. The inventors of the present invention compared results of Raman spectrometry for a normal cartilage and a cartilage in an initial stage of degeneration, and found out 'Index (c): composition and total amount of glycosaminoglycan' and 'Index (d): level of glycosylation of protein and the total amount of glycosaminoglycan for determining the degree of degeneration of cartilage in the glycosaminoglycan region.
<Index (c)>

Index (c) is a composition of glycosaminoglycan (GAG) and the total amount of GAG. A cartilage includes chondroitin sulfate (CS), hyaluronic acid (HA), heparan sulfate (HS), and the like as glycosaminoglycan, and a composition ratio thereof and the total amount of GAG varies according to the degree of degeneration of cartilage. As it will be described later in the examples, a peak of the glycosaminoglycan region is presumed to change in two stages with the degeneration of cartilage. In a first stage, due to the above-mentioned change (loosening) in the collagen secondary structure, HA included abundantly in a joint fluid is susceptible to move inside the cartilage, and moreover, HA being highly hydrophilic, is accumulated inside cartilage structure having a high hydration level. Furthermore, in response to extracellular matrix degeneration, hyaluronic acid synthesis from the cartilage cell is accelerated, and as a result, a content ratio CS/HA decreases (an accumulation—biosynthesis stage, up to around two weeks after the OA surgery). Next, as the degeneration of cartilage progresses further in a second stage, due to a degradation of GAG and a decrease in a GAG secretion from the cartilage cell, while the content ratio of CS/HA returns to a value before the OA surgery, a band intensity of an overall GAG region decreases (a degradation stage). Although the accumulation—biosynthesis stage of hyaluronic acid is a reversible reaction, and it is presumed that as it reaches the degradation stage, an irreversible state is assumed gradually.

In Index (c), a preferable aspect of a composition of GAG is a ratio of content of chondroitin sulfate and hyaluronic acid in cartilage. As a band derived from chondroitin sulfate, a band observed near the wavenumber 1065 cm$^{-1}$, favorably in a range from 1060 cm$^{-1}$ to 1070 cm$^{-1}$, is preferable. The band near the wavenumber 1065 cm$^{-1}$ is a band derived from $OSO_3^-$ symmetric stretching, and since hyaluronic acid does not have a sulfate group, it is possible to make it an index specific to chondroitin sulfate. Whereas, as a band derived from hyaluronic acid, a band observed near the wavenumber 1123 cm$^{-1}$, favorably in a range from 1118 cm$^{-1}$ to 1128 cm$^{-1}$, is preferable. The band near the wavenumber 1123 cm$^{-1}$ is a band derived from bending vibration of a C—OH group and a C—H group, and it is possible to make it as an index specific to hyaluronic acid.

In Index (c), as the total amount of GAG, a sum of integrated intensity of a peak of the GAG region in a range of wavenumbers from 1000 cm$^{-1}$ to 1200 cm$^{-1}$ for example, can be used.

As an aspect of a value representing the composition of GAG in Index (c), a value which reflects a ratio of the content of chondroitin sulfate and the content of hyaluronic acid in cartilage is preferable. For example, a ratio of an integrated intensity of a peak near 1065 cm$^{-1}$ and an integrated intensity of a peak near 1123 cm$^{-1}$ which reflects this ratio in Raman spectrometry is preferable, and a ratio ($I_{1065}/I_{1123}$) of an integrated intensity ($I_{1065}$) of a peak of a range from 1060 cm$^{-1}$ to 1070 cm$^{-1}$ and an integrated intensity ($I_{1123}$) of a peak of a range from 1118 cm$^{-1}$ to 1128 cm$^{-1}$ is more preferable. As it will be described later in the examples, in a cartilage two weeks after the OA surgery for inducing joint instability, while $I_{1065}$ derived from chondroitin sulfate decreased, $I_{1123}$ derived from hyaluronic acid increased, and $I_{1065}/I_{1123}$ decreased. However, in a cartilage four weeks after the OA surgery, while the integrated intensity of a peak of the overall glycosaminoglycan region decreased to be near half of that for the normal cartilage, the $I_{1065}/I_{1123}$ returned to a state close to a value for the normal cartilage. Therefore, the value of $I_{1065}/I_{1123}$ and a sum of the integrated intensities of the GAG region in the range of wavenumbers from 1000 cm$^{-1}$ to 1200 cm$^{-1}$ can be preferably used as a value representing Index (c). Although it is not restricted in particular, for example, when $I_{1065}/I_{1123}$ for cartilage of a subject is not more than 0.5 times of the reference value for the normal cartilage, it is judged to be at the first stage of degeneration. Moreover, when $I_{1065}/I_{1123}$ is nearly same as the reference value for the normal cartilage (between 0.7 times to 1.2 times for example), and the integrated intensity of the peak of the overall GAG region is not more than approximately 0.5 times of the reference value for the normal cartilage, it is judged to be at the second stage of degeneration.

<Index (d)>

Index (d) is a level of glycosylation of protein (also simply referred to as 'glycosylation') and a total amount of GAG. In a case of cartilage, the glycosylation occurs mainly as a high-mannose glycosylation to N atoms of amide, it is to be evaluated according to the peak near 1165 cm$^{-1}$ derived from an exocyclic —C—O—C—bond. The N-linked glycosylation is a site-specific reaction of an enzyme in which, a sugar chain (a glycosyl donor) is linked with a hydroxyl group or other functional group consisting of another molecule (a glycosyl acceptor such as protein). In the case of cartilage, an exocyclic oxygen-bridged bond (—C—O—C—) exists in proteoglycan and a long unbranched chain of glycosaminoglycan. Index (d), similarly as Index (c), reflects a two-stage degeneration of a cartilage. As it will be described later in the examples, in a cartilage two weeks after the OA surgery for inducing the joint instability (first stage), the integrated intensity of the peak near 1165 cm$^1$ increases substantially, and reflects an increase in the glycosylation due to the high-mannose glycosylation. Next, as the degeneration of cartilage cell progresses further in the second stage, while the integrated intensity of the peak near 1165 cm$^{-1}$ returns to a value close to the value before the OA surgery, the band intensity of the overall GAG region decreases due to the degradation of GAG and the decrease in the GAG secretion from the cartilage cell.

In Index (d), a sum of the integrated intensities of the peak of the GAG region in the range of wavenumbers from 1000 cm$^{-1}$ to 1200 cm$^{-1}$ for example, can be used as the total amount of GAG.

As a preferable aspect indicating the level of glycosylation of protein of Index (d), a value obtained by normalizing the integrated intensity of the peak near 1165 cm$^{-1}$ by the integrated intensity of a peak near 850 cm$^{-1}$ representing C—C stretching vibration of a backbone of protein is preferable, and it is preferable that it is a ratio ($I_{1165}/I_{850}$) of the integrated intensity ($I_{1165}$) of the peak of the range from 1160 cm$^{-1}$ to 1170 cm$^{-1}$ and an integrated intensity of a peak of a range from 845 cm$^{-1}$ to 855 cm$^{-1}$. As it will be described later in the examples, ($I_{1165}/I_{850}$) increased in a cartilage two weeks after the OA surgery for inducing joint instability, but decreased thereafter. This indicates that a structure of N-linked glycosylation changes with the progression of degeneration of cartilage. However, in a cartilage four weeks after the OA surgery, while the integrated intensity of the peak of the overall glycosaminoglycan region decreased to nearly half of that for the normal cartilage, $I_{1165}/I_{850}$ returned close to the value for the normal cartilage. Therefore, the value of $I_{1165}/I_{850}$ and a sum of integrated intensities of the GAG region in the range of wavenumbers from 1000 cm$^{-1}$ to 1200 cm$^{-1}$ can be preferably used as the value representing Index (d). Although it is not restricted in particular, for example, when $I_{1165}/I_{850}$ for cartilage of a subject is twice or more than twice the reference value for the normal cartilage, it is judged to be at the first stage of degeneration. Moreover, when $I_{1065}/I_{1123}$ is nearly same as the reference value for the normal cartilage (between 0.7 to 1.2 times for example), and the integrated intensity of the peak of the overall GAG region is not more than approximately 0.5 time of the reference value for the normal cartilage, it is judged to be at the second stage of degeneration.

According to an aspect of the present embodiment, it is preferable to combine Index (c) and Index (d). By combining Index (c) and Index (d), it is possible to determine the degree of degeneration of a cartilage in more detail on the basis of a change in glycosaminoglycan. As an aspect of the present embodiment, for example, when the $I_{1065}/I_{1123}$ of the cartilage of a subject is not more than 0.5 times the reference value for the normal cartilage, and $I_{1165}/I_{850}$ is twice or more than twice the reference value for the normal cartilage, the cartilage of a subject is judged to be at the first stage of degeneration. Whereas, for example, when $I_{1065}/I_{1123}$ and $I_{1165}/I_{850}$ of the cartilage of a subject are nearly same as the reference value for the normal cartilage (between 0.7 times to 1.2 times for example), and the integrated intensity of the peak of the overall GAG region is not more than approximately 0.5 times of the reference value for the normal cartilage, the cartilage of a subject is judged to be at the second stage of degeneration.

The cartilage degeneration analyzer of the present embodiment has a processor which includes an index calculator configured to calculate a value which represents at least one index selected from a group consisting of Indices (a) to (d). It is preferable that the index calculator calculates values representing two or more than two indices selected from the group consisting of Indices (a) to (d), and may calculate values representing all the indices. By combining a plurality of indices, it is possible to determine in more detail as to at which stage the degeneration of cartilage is. Moreover, a plurality of values which reflect one index may be calculated.

The analyzer of the present embodiment, according to an aspect, is capable of detecting a degree of regeneration of a cartilage tissue on the basis of a Raman spectrum of a cartilage obtained by irradiating excitation light to a part of cartilage of a subject, upon administering a therapeutic medication to the subject having a degenerated cartilage. As it will be described later in the examples, the inventors of the present invention found out that the Indices (a) to (d) become indices for regeneration of a cartilage tissue which is affected.

As an aspect of the apparatus of the present embodiment, a judging unit having the processor which includes the index calculator, and the judging section will be described below by using FIG. 9.

Figure 9:
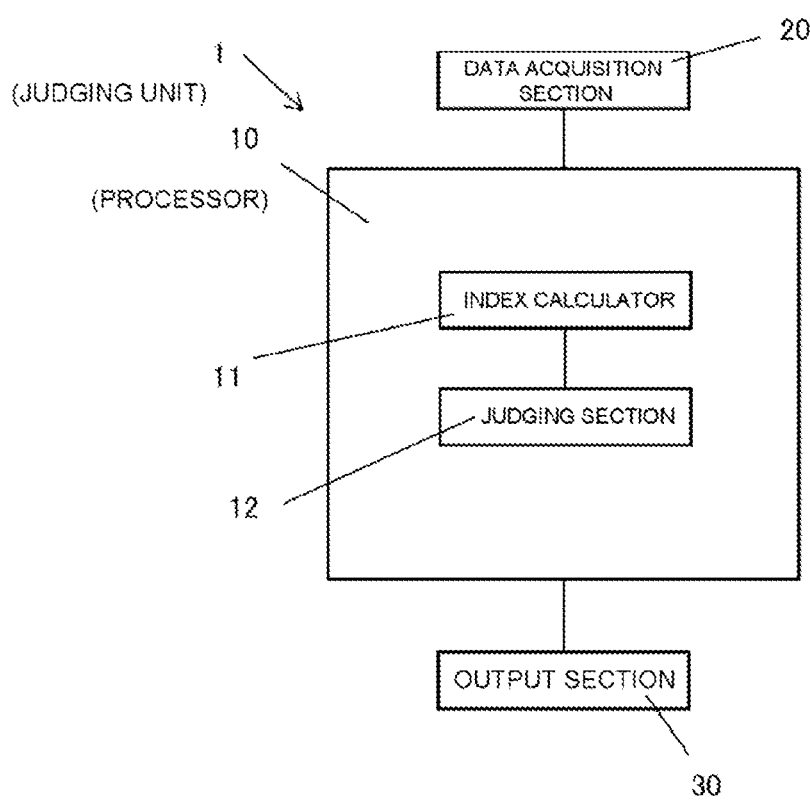
FIG. 9 is a diagram showing an example of a configuration of a judging unit of the present embodiment.

A judging unit 1 of the present embodiment, may include for example, a data acquisition section 20 which acquires spectral data, a processor 10 which is configured to calculate a value representing an index on the basis of the data acquired and to determine the degree of degeneration of cartilage on the basis of that value, and an output section 30 which outputs a result of the judgment made (FIG. 9).

For instance, the data acquisition section 20 may be connectable to a spectrometer or an endoscope, or may have been integrated with a spectrometer or an endoscope. It is preferable that the processor 10 has an index calculator 11 which is configured to calculate the value representing the index, and a judging section 12 which is configured to determine the degree of degeneration of cartilage on the basis of the value calculated by the index calculator. The processor 10 may be, for instance, a general-purpose computer or a computer for exclusive use having a CPU (Central Processing Unit), a memory, and an interface, and with an appropriate computer program (for example, a computer program which makes computer execute a judging method disclosed in the present specification) installed in the memory. In this case, the index calculator 11 and the judging section 12 may exist as a function performed by the processor 10. The computer may be a so-called one-chip microcomputer having hardware such as a CPU, a ROM, a RAM, and an interface (I/F), and a computer program installed. Or a processing carried out by the processor 10 may be implemented by hardware of a logic circuit, or may be in combination with the computer program.

Regarding the computer program, the execution may be carried out singularly or in plurality. The computer program may be stored in a storage medium which is computer-readable. The storage medium in which the computer program is stored may be a non-transient storage medium. The non-transient storage medium is not restricted in particular, and may be a storage medium such as a memory card and a CD-ROM for example. The computer program stored in the storage medium can be installed in a computer via appropriate reader. Examples of the appropriate reader are a card reader in a case in which the storage medium is a memory card, and a CD drive in a case in which the storage medium is a CD-ROM. The computer program may be a computer program which is to be downloaded fully or partially from an external device whenever necessary, via an arbitrary network.

In the judging section 12, for example, the value calculated by the index calculator 11 and the value (reference value) representing each index of the normal cartilage are compared, and a judgment of whether or not the cartilage is degenerated is made and the degree of degeneration is determined. The reference value, although is not restricted in particular, in a case in which the subject is a human, may be set including information such as age, sex, height, and weight, or, may be a value calculated on the basis of an average measured value of a plurality of healthy subjects. The judging section 12 may have a storage section storing data such as data of reference values and data of index values calculated when the degeneration of cartilage progressed. Moreover, the judging section 12 may determine the degree of degeneration of cartilage on the basis of a combination of values representing the plurality of indices calculated by the index calculator 11.

The output section 30 may include for example, a display, a printer, and a speaker, and a destination of output may be another server or device connected over the network.

The judging unit may further include an input section which receives input operations from a user. The input operations from the user may include operations such as an input operation for each setting related to an operation of the judging unit and an input operation for executing the computer programs. The input section may be an arbitrary input device such as a key board, a mouse, a pointing device, and a touch panel.

The judging unit which calculates the value representing the index on the basis of the spectral data and determines the degree of degeneration of cartilage on the basis of that value has heretofore been described, and an arrangement can also be made such that the user determines the degree of degeneration of cartilage. In this case, the unit does not need to have a function (or the judging section) which determines the degree of degeneration of cartilage, and the processor can be configured to output the value calculated by the index calculator for example to the output section.

The analyzer of the present embodiment can be used for diagnosis of a disease in which articular cartilage is degenerated or a disease in which the progression of the degeneration is predicted. An example of the disease in which the articular cartilage is degenerated or the disease in which the progression of the degeneration is predicted is osteoarthritis (OA). Osteoarthritis is induced due to factors such as an external injury such as ligamentous injury and medial meniscus injury, aging, obesity, a hereditary factor, and an environmental factor. Moreover, the analyzer of the present embodiment, by treating a cartilage affected by osteoarthritis (OA), can also be used for diagnosis of a degree of recovery of the cartilage.

<Diagnostic Apparatus and Diagnostic Aid Apparatus>

An aspect of the present embodiment relates to a diagnostic apparatus or a diagnostic aid apparatus which includes the analyzer. The diagnostic apparatus or the diagnostic aid apparatus of the present embodiment is preferably an apparatus for diagnosis of or an apparatus for aiding diagnosis of a disease in which the articular cartilage is degenerated, and more preferably an apparatus for diagnosis of or an apparatus for aiding diagnosis of osteoarthritis (OA). The diagnostic (aid) apparatus, although is not restricted in particular, may include for example, an excitation-light source, an instrument which is operably linked to the excitation-light source, and the analyzer. The instrument which is operably linked to the excitation-light source includes for example, an illuminator which irradiates the excitation light incident from the excitation light source to cartilage of a subject, a light receiving section which receives scattered light from the cartilage, and a detecting section which detects Raman spectrum from the scattered light received by the light receiving section. On the basis of the Raman spectrum detected by the detecting section, the degree of degeneration of cartilage is determined by using the analyzer, and diagnosis of a predefined disease can be made. The diagnostic apparatus or the diagnostic aid apparatus of the present embodiment may include an endoscope.

<Method for Determining Degree of Cartilage Degeneration>

An aspect of the present embodiment relates to a method for determining a degree of degeneration of a cartilage, comprising calculating on the basis of a Raman spectrum obtained by Raman spectrometry in which excitation light is irradiated to cartilage of a subject, a value representing at least one index from a group consisting of Index (a): secondary structure of collagen, Index (b): hydration level of collagen, Index (c): composition and total amount of glycosaminoglycan, and Index (d): level of glycosylation of protein and total amount of glycosaminoglycan, and determining a degree of degeneration of cartilage on the basis of the value calculated. The description of the analyzer applies to each index of the method of determining.

<Method for Determining a Degree of Regeneration>

An aspect of the present embodiment relates to a method for determining a degree of regeneration of cartilage comprising, calculating on the basis of a Raman spectrum from cartilage obtained by irradiating a part of cartilage of a subject administered with the test substance with excitation light, a value representing at least one index from a group consisting of Index (a): secondary structure of collagen, Index (b): hydration level of collagen, Index (c): composition and total amount of glycosaminoglycan, and Index (d): level of glycosylation of protein and total amount of glycosaminoglycan, and determining the degree of regeneration of cartilage on the basis of the value calculated. The description of the analyzer applies to each index of the method for determining the degree of regeneration of cartilage. In the method for determining the degree of regeneration of cartilage, treatment may be carried out by a method such as surgery of the subject instead of administering treatment medication or in addition to administering treatment medication.

An aspect of the present embodiment relates to a method for evaluating a drug action (drug action evaluation method) of a test substance, comprising calculating on the basis of a Raman spectrum from cartilage obtained by irradiating a part of cartilage of a subject administered with the test substance with excitation light, a value representing at least one index from a group consisting of Index (a): secondary structure of collagen, Index (b): hydration level of collagen, Index (c): composition and total amount of glycosaminoglycan, and Index (d): level of glycosylation of protein and total amount of glycosaminoglycan, and evaluating a drug action of a test substance on the basis of the value calculated.

The description of the analyzer is applicable to Indices (a) to (d) in the drug action evaluation method. Index (a) to Index (d) determine the degree to which the progression of cartilage degeneration is inhibited by administering the test substance, and the degree to which the cartilage is regenerated, and can be made indices for the drug action of the test substance.

In the present specification, 'test substance' refers to any substance subject to evaluation of whether or not it becomes a therapeutic substance and/or a preventive medicine for a disease in which cartilage is degenerated due to osteoarthritis. The test substances are not restricted in particular, and include low-molecular compounds, nucleic acids, or polypeptides. The low-molecular compounds, the nucleic acids, and the polypeptides may be those obtained by extracting and refining from natural products, or may be those synthesized artificially. Moreover, the test substance, without being restricted to a refined test substance, may be an unrefined test substance. Furthermore, the test substance, without being restricted to a novel substance, may be a known test substance or an improved test substance. As an aspect of the test substance, the nucleic acid may be the one which can be used for nucleic acid delivery and which is prepared together with a pharmaceutically permissible nucleic acid-delivering carrier.

A method of administration, a dosage amount, a dosage frequency etc. are not restricted. As a method of administration, for instance, it can be administered either orally or parenterally. Examples of parenteral administration are, injection administration, nasal administration, pulmonary administration, and transdermal administration. Moreover, the administration may be by a drug-delivery system.

The inventors of the present invention administered mRNA encoded with Runx1 (mRNA/Runx1) which is known as an effective transcription factor in a treatment of osteoarthritis, into joint of a mouse induced with joint instability by OA surgery, and carried out Raman spectrometry for the cartilage. It could be confirmed that each of the values representing Indices (a) to (d) one week after administering mRNA/Rnux1 was restored to about the same level as for the normal cartilage. Moreover, the drug action evaluating method of the present embodiment can be used for screening of therapeutic medication.

EXAMPLES

The present embodiment will be described below in detail by referring to the examples, but the present embodiment is not limited to these examples.

<Raman Spectrometry>

Raman spectrometry in the examples was performed as described below.

Raman spectrometry was performed by a high-spectral resolution Raman microprobe spectrometer (T-64000 manufactured by HORIBA Jovin Yvon Co. Ltd.) which is operated based on backscattering geometry. The Raman spectrometry was performed by using a diode laser (SOC Juno manufactured by Showa optronics Co. Ltd.) of wavelength 532 nm as excitation light, with an output of approximately 10 mW on a cartilage surface. As a confocal configuration of a laser probe, a pinhole diameter of a cross slit was fixed to be 100 μm corresponding to an objective lens of 100 times magnification. Calibration was carried out such that a penetration depth of the laser reached is of order of approximately 10 μm. An unpolarized Raman spectrum was averaged by measuring three times consecutively at each selected position. Spectral resolution beyond 0.15 cm$^{-1}$ was obtained by using a grating of 1800 lines/mm, and by recording a signal selected from a neon lamp for internal calibration of the spectrometer. The measurement was carried out at an ambient temperature of 22° C. An automatic fitting algorithm included in a commercially available calculation package (LabSpec 5, manufactured by HORIBA Jovin Yvon Co. Ltd.) was used for background subtraction and spectral deconvolution. In the spectral deconvolution, a spectral sub-band was fitted (matched) by using a mixed Gaussian-Lorentzian (Voigtian) curve.

For a band obtained by Raman spectrometry, the integrated intensity of each wavenumber region was calculated by using an analysis software (Origin 9.1, OriginLab Co., Northampton, MA, USA). One-way analysis of variance (ANOVA) was carried out for numerical values obtained, and it was deemed to have a significant difference at a level of $p < 0.05$. An unpaired bilateral student's t-test was carried out for comparing a change between (in) same parameters for each control group.

<OA surgery>

12 three months old Balb-c mice were procured, and medial meniscus (MM) and medial collateral ligament (MCL) of a right knee joint of the mice were cut off and a surgery (OA surgery) for inducing joint instability was performed. The mice were euthanized one week, two weeks, three weeks, four weeks after the OA surgery, and one week after administering mRNA/Runx1 in mRNA group (described later) respectively. A lower limb was dismembered at the knee joint, and a tibial cartilage surface was exposed. With a right medial tibial cartilage as a sample induced with osteoarthritis and a left medial tibial cartilage as a control sample which is not affected by osteoarthritis (normal tibial cartilage), measurement and analysis by ex vivo Raman spectroscopy. Hereinafter, 'medial tibial cartilage' will simply be referred to as 'cartilage'.

<Administering mRNA/Runx1>

As a therapeutic medication for OS cartilage, mRNA encoded with Runx1 (mRNA/Runx1) which is a therapeutic cartilage-inducible transcription factor was mixed with a cationic polymer (PEG-PAsp (DET)) and a micellar carrier (mRNA concentration 50 µg/ml) was prepared. 20 µl of the therapeutic medication prepared was administered to (mRNA group) the joint of the mouse four weeks after the OA surgery.

<Raman Spectrum of Cartilage>

A Raman spectrum of a normal cartilage is shown in FIG. 1a, a Raman spectrum of a cartilage two weeks after the OA surgery is shown in FIG. 1b, and a Raman spectrum of a cartilage four weeks after the OA surgery is shown in FIG. 1c. The Raman spectra are spectra normalized by a C—C stretching signal of a protein backbone of approximately 850 $cm^{-1}$. In this Raman spectra, a tertiary amide region which reflects the secondary structure of collagen and the hydration level of collagen (region of wavenumbers in a range from 1170 $cm^{-1}$ to 1500 $cm^{-1}$) and a glycosaminoglycan region which reflects the composition of glycosaminoglycan and the level of glycosylation of protein (region of wavenumbers in a range from 1000 $cm^{-1}$ to 1200 $cm^{-1}$) were analyzed in detail.

<Analysis of Tertiary Amide Region>

Figure 2:
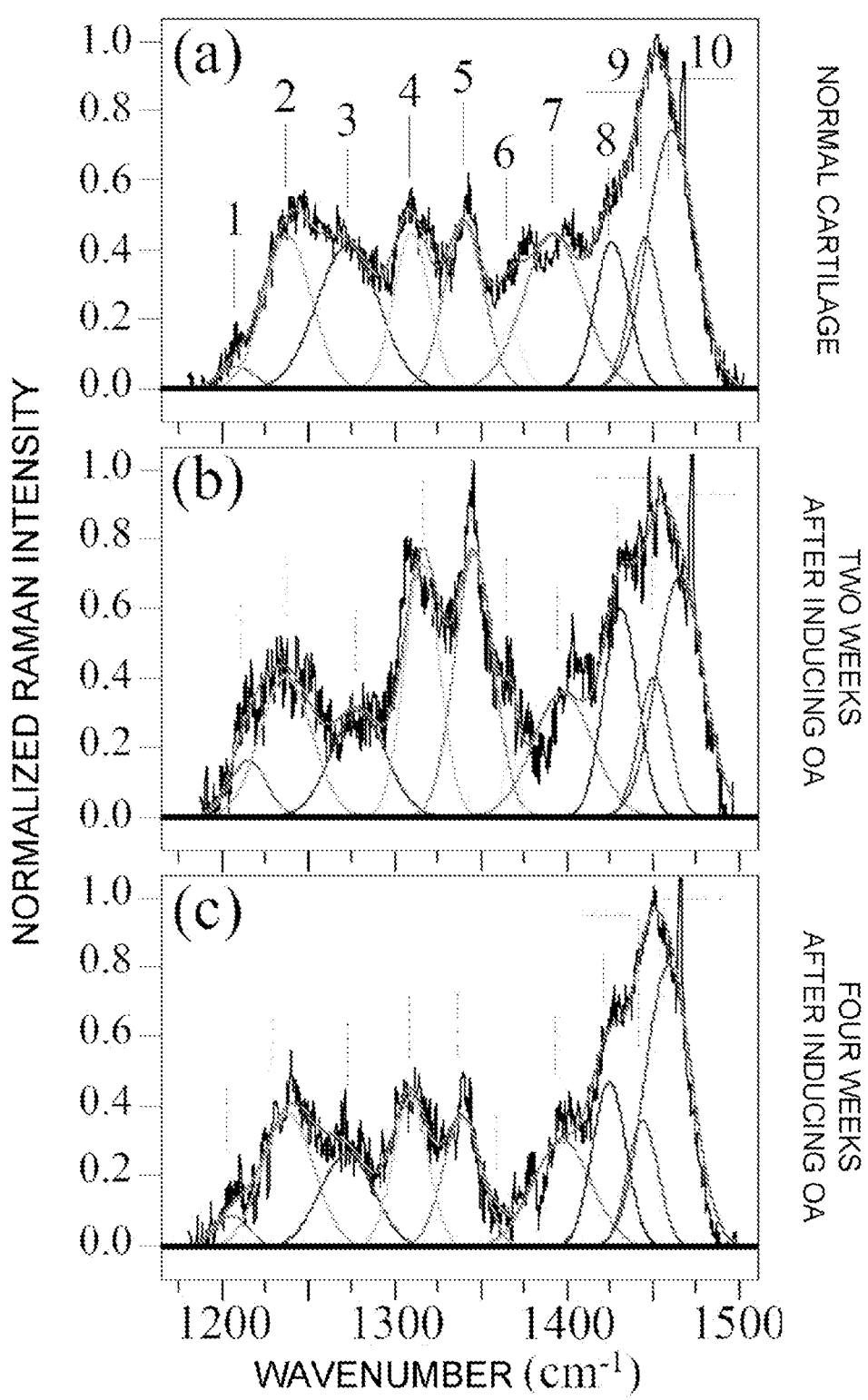
FIG. 2a is a diagram showing a Raman spectrum of a tertiary amide region of a normal cartilage.
FIG. 2b is a diagram showing a Raman spectrum of a tertiary amide region of a cartilage two weeks after the OA surgery.
FIG. 2c is a diagram showing a Raman spectrum of a tertiary amide region of a cartilage four weeks after the OA surgery.

In the tertiary amide region of wavenumbers in the range of 1170 $cm^{-1}$ to 1500 $cm^{-1}$, ten sub bands were selected by deconvolution (FIG. 2). A chemical structure from which the peak and wavenumbers of these sub bands are derived are shown in table 1.

TABLE 1

| Band No. | Wavenumber ($cm^{-1}$) | Chemical structure from which the peak is derived |
|---|---|---|
| 1 | 1205 | C—$C_6H_5$ stretching vibration |
| 2 | 1240 | tertiary amide (random coil) |
| 3 | 1270 | tertiary amide (α-helix) |
| 4 | 1312 | N—H vibration and C=O of hydration amide (α-helix) |
| 5 | 1340 | NαH vibration and C=O of hydration amide (α-helix) |
| 6 | 1365 | annular structure and stretching vibration of C—N |
| 7 | 1391 | $CH_2$ deformation vibration |
| 8 | 1429 | $CH_2$ bending vibration |
| 9 | 1446 | methyl deformation vibration |
| 10 | 1459 | methylene deformation vibration |

Band 2 and band 3 reflect a secondary structure of collagen protein. Band 2 is derived from random-coil collagen and band 3 is derived from α-helix structure. Moreover, both band 4 and band 5 are derived from α-helix structure, and reflect a hydration level thereof.

A Raman spectrum of a tertiary amide region of a normal cartilage is shown in FIG. 2a, a Raman spectrum of a tertiary amide region of a cartilage two weeks after the OA surgery is shown in FIG. 2b, and a Raman spectrum of a tertiary amide region of a cartilage four weeks after the OA surgery is shown in FIG. 2c.

Figure 4:
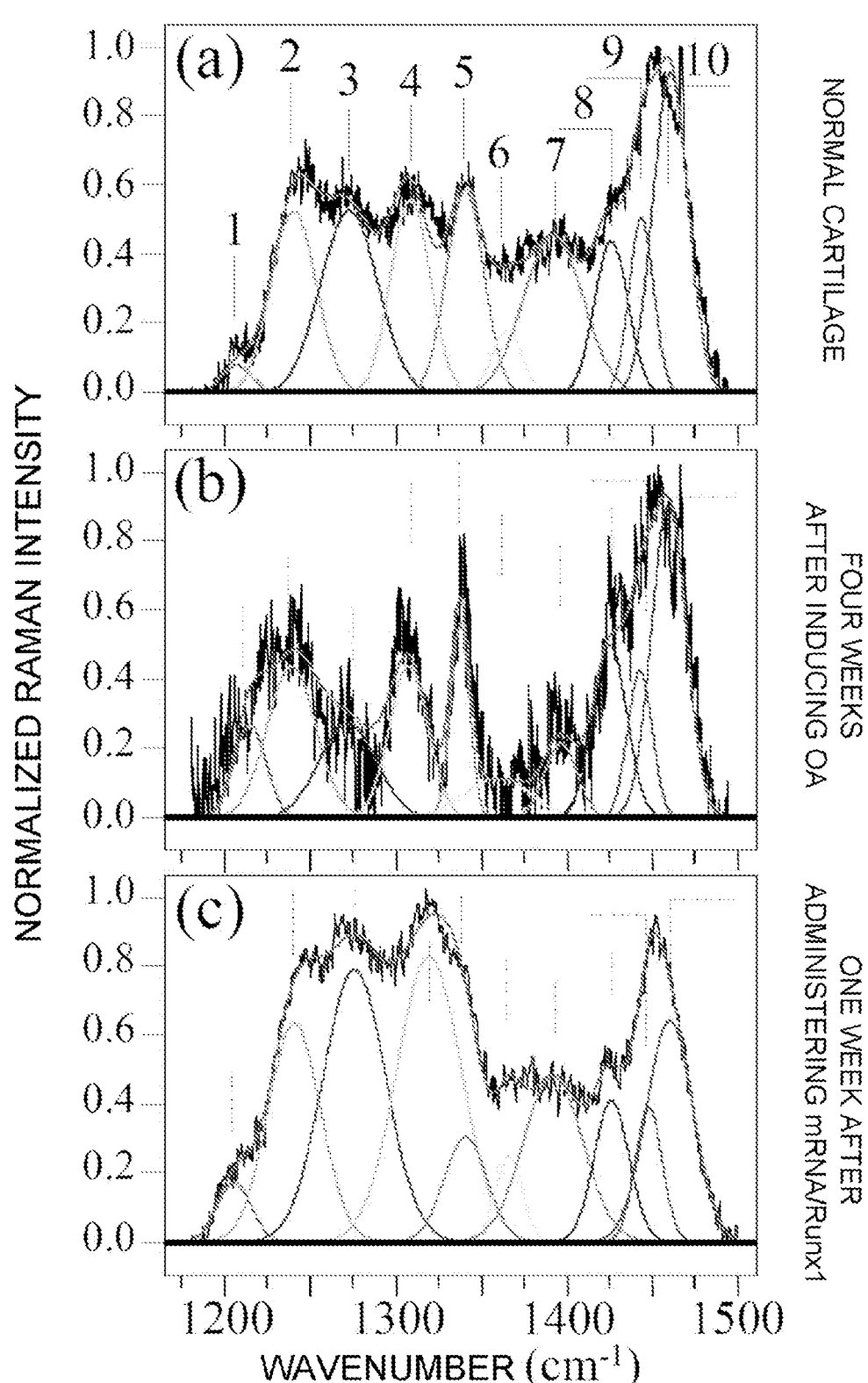
FIG. 4a is a diagram showing a Raman spectrum of a tertiary amide region of a normal cartilage.
FIG. 4b is a diagram showing a Raman spectrum of the tertiary amide region of the cartilage four weeks after the OA surgery.
FIG. 4c is a diagram showing a Raman spectrum of a tertiary amide region of a cartilage one week after administering mRNA subjected to Runx1 encoding in four weeks after the OA surgery.

A Raman spectrum of a tertiary amide region of a normal cartilage is shown in FIG. 4a, a Raman spectrum of a tertiary amide region of a cartilage four weeks after the OA surgery is shown in FIG. 4b, and a Raman spectrum of a tertiary amide region of a cartilage one week after administering mRNA/Runx1 in four weeks after the OA surgery is shown in FIG. 4c.

Figure 6:
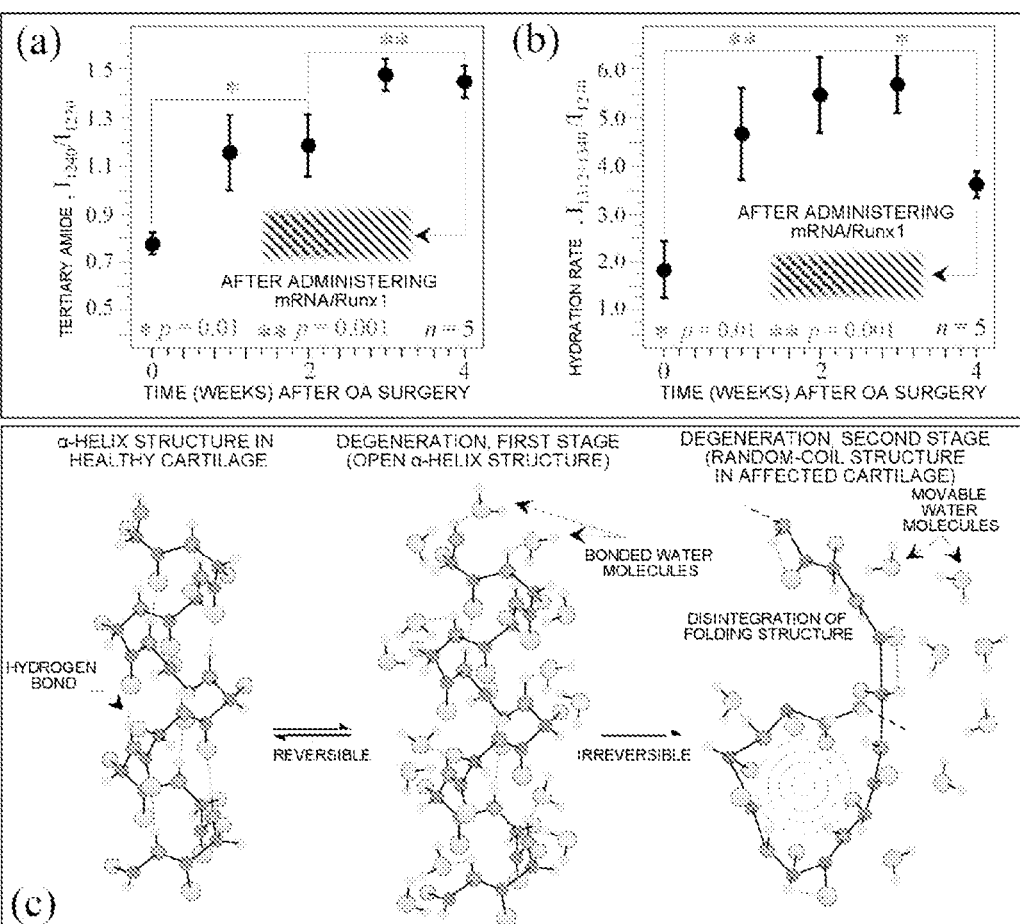
FIG. 6a is a diagram showing a relationship of time elapsed after the OA surgery and a Raman spectral intensity ratio ($I_{1240}/I_{1270}$)
FIG. 6b is a diagram showing a relationship of time elapsed after the OA surgery and a Raman spectral intensity ratio ($I_{1312+1340}/I_{1270}$)
FIG. 6c is a diagram showing schematically a change in a secondary structure of collagen in the degeneration of cartilage.

A relationship of time after the OA surgery and a predefined Raman spectral ratio in the tertiary amide region is shown in FIG. 6 (FIG. 6a, FIG. 6b, and FIG. 6c). FIG. 6a shows a relationship of time after the OA surgery and a spectral intensity ratio ($I_{1240}/I_{1270}$) representing an abundance ratio of random-coil collagen and α-helix collagen and FIG. 6b shows a relationship of time after the OA surgery and a spectral intensity ratio ($(I_{1312)+1340}/I_{1270}$) representing a hydration level of collagen. Moreover, in FIG. 6a and FIG. 6b, a hatched portion in a graph shows each spectral intensity ratio one week after administering mRNA/Runx1.

While a value of $I_{1240}/I_{1270}$ increased with elapsing of time after the OA surgery (FIG. 6a), $I_{1312+1340}/I_{1270}$ became large after two weeks, and decreased thereafter (FIG. 6b). This indicates that the degeneration of cartilage progresses in two stages. FIG. 6c is a diagram showing schematically a change in a secondary structure of collagen during degeneration of cartilage in two stages. In a first stage, because a hydrogen bond inside the α-helix structure recedes gradually and an open α-helix structure is formed by hydrogen bonding with an external water molecule, $I_{1240}/I_{1270}$ and $I_{1312+1340}/I_{1270}$ increase (up to around two weeks after the OA surgery). In this stage, the α-helix structure is presumed to change reversibly. However, as the cartilage degeneration progresses further, the hydrogen bond at the interior almost ceases to exist, and while the α-helix structure is disintegrated irreversibly, and a proportion of the random-coil structure increases and $I_{1240}/I_{1270}$ increases, because the external water molecule returns to a movable state, $I_{1312+1340}/I_{1270}$ is presumed to decrease (second stage, three to four weeks after the OA surgery).

Moreover, in FIG. 6a and FIG. 6b, each spectral intensity ratio one week after administering mRNA/Runx1 was restored to a value close to that for the normal cartilage. Thus, it was confirmed that $I_{1240}/I_{1270}$ and $I_{1312+1314}/I_{1270}$ reflected the fact that the cartilage-inducing ability of chondrocytes was activated by mRNA/Runx1, resulting in the restoration and reformation of collagen molecular structure.

<Analysis of Glycosaminoglycan Region>

Figure 3:
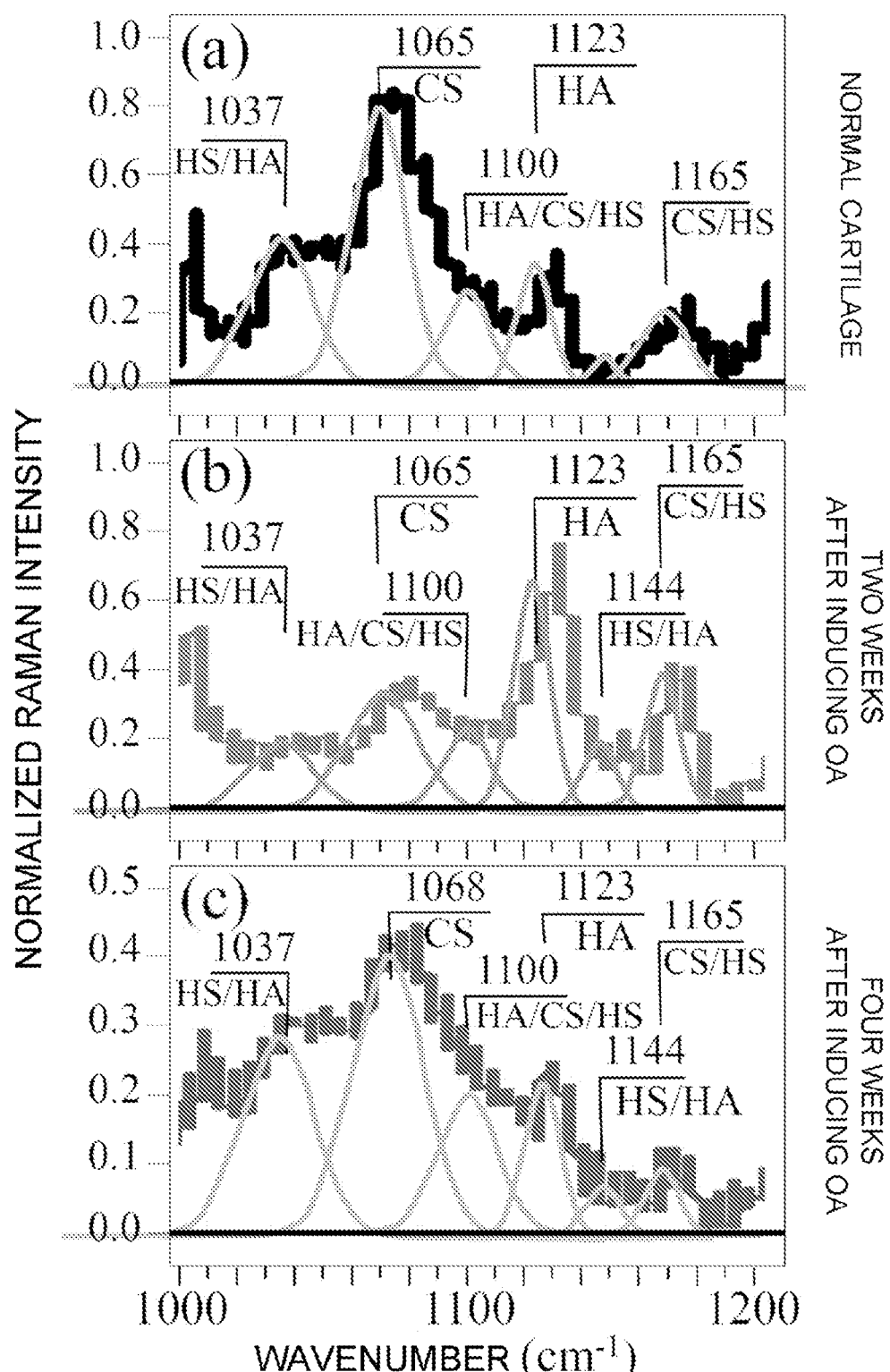
FIG. 3a is a diagram showing a Raman spectrum of a glycosaminoglycan region of a normal cartilage.
FIG. 3b is a diagram showing a Raman spectrum of a glycosaminoglycan region of a cartilage two weeks after the OA surgery.
FIG. 3c is a diagram showing a Raman spectrum of a glycosaminoglycan region of a cartilage four weeks after the OA surgery.

In the glycosaminoglycan region of wavenumbers in a range from 1000 $cm^{-1}$ to 1200 $cm^{-1}$, by deconvolution, six sub bands derived from chondroitin sulfate (CS), hyaluronic acid (HA), and heparan sulfate were selected (FIG. 3).

A Raman spectrum of a glycosaminoglycan region of a normal cartilage is shown in FIG. 3a, a Raman spectrum of a glycosaminoglycan region of a cartilage two weeks after the OA surgery is shown in FIG. 3b, and a Raman spectrum of glycosaminoglycan region of a cartilage four weeks after the OA surgery is shown in FIG. 3c.

Figure 5:
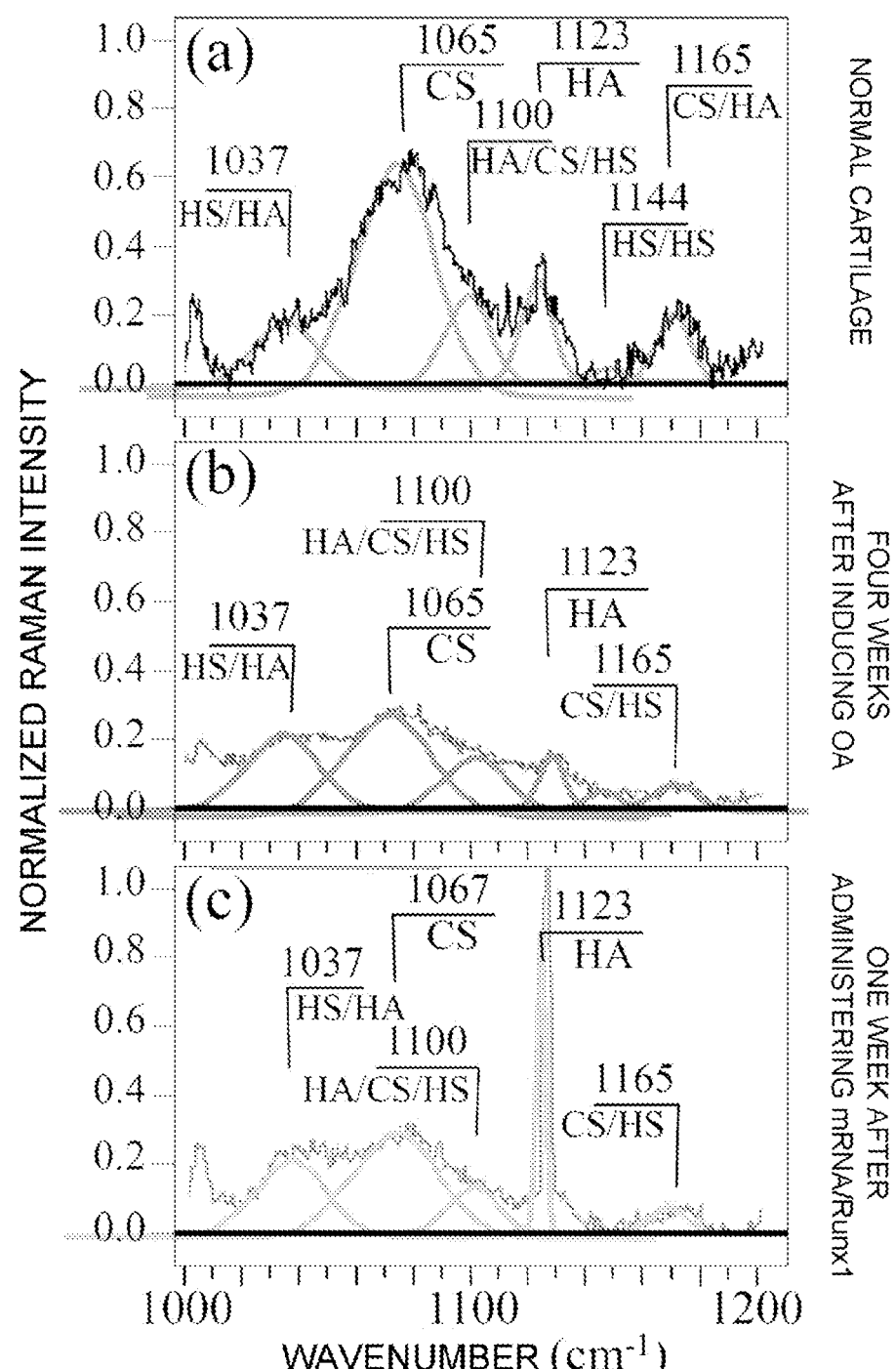
FIG. 5a is a diagram showing a Raman spectrum of a glycosaminoglycan region of a normal cartilage.
FIG. 5b is a diagram showing a Raman spectrum of a glycosaminoglycan region of a cartilage four weeks after the OA surgery.
FIG. 5c is a diagram showing a Raman spectrum of a glycosaminoglycan region of a cartilage one week after administering mRNA subjected to Runx1 encoding in four weeks after the OA surgery.

A Raman spectrum of a glycosaminoglycan region of a normal cartilage is shown in FIG. 5a, a Raman spectrum of a glycosaminoglycan region of a cartilage four weeks after the OA surgery is shown in FIG. 5b, and a Raman spectrum of a glycosaminoglycan region of a cartilage one week after administering mRNA encoded with Runx1 four weeks after the OA surgery is shown in FIG. 5c.

Figure 7:
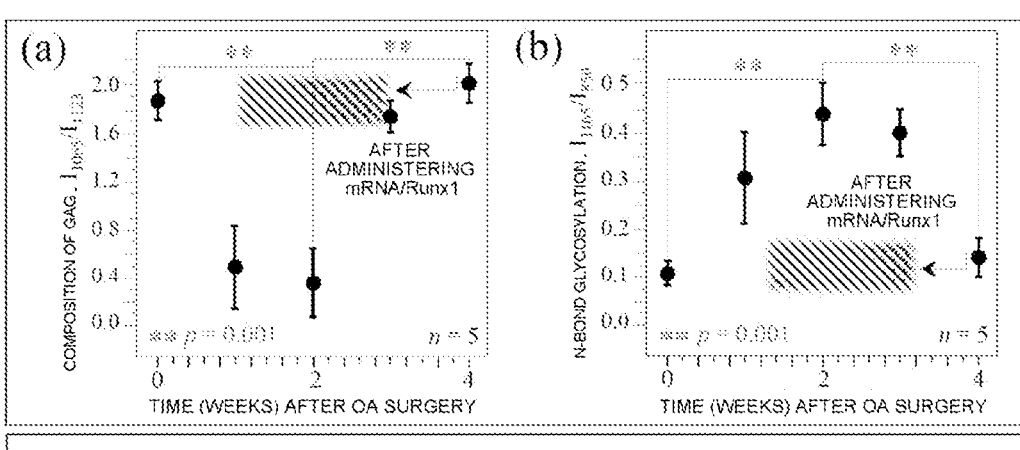
FIG. 7a is a diagram showing a relationship of time elapsed after the OA surgery and a Raman spectral intensity ratio ($I_{1065}/I_{1123}$)
FIG. 7b is a diagram showing a relationship of time elapsed after the OA surgery and a Raman spectral intensity ratio ($I_{1165}/I_{850}$)
FIG. 7c is a diagram showing schematically a change in glycosaminoglycan during the degeneration of cartilage.
Figure 7:
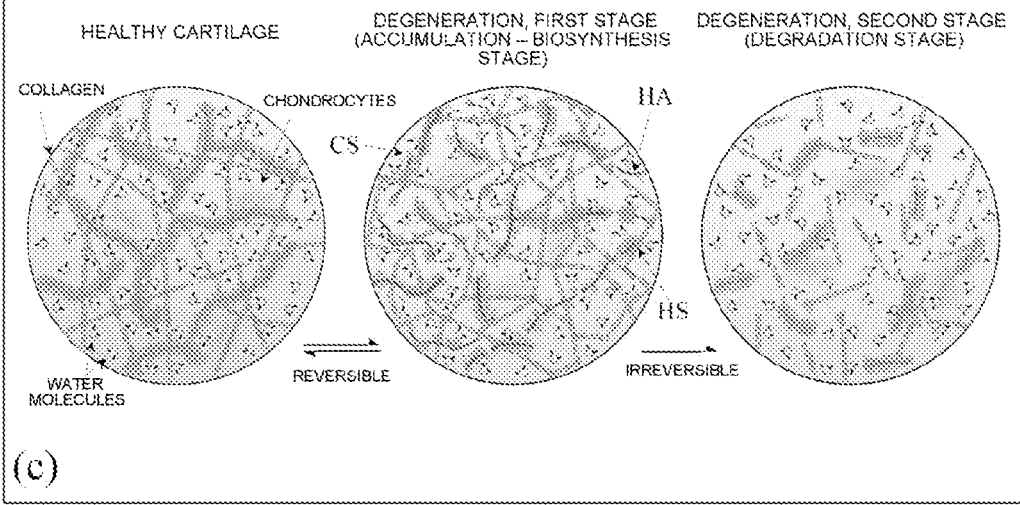
Figure 8:
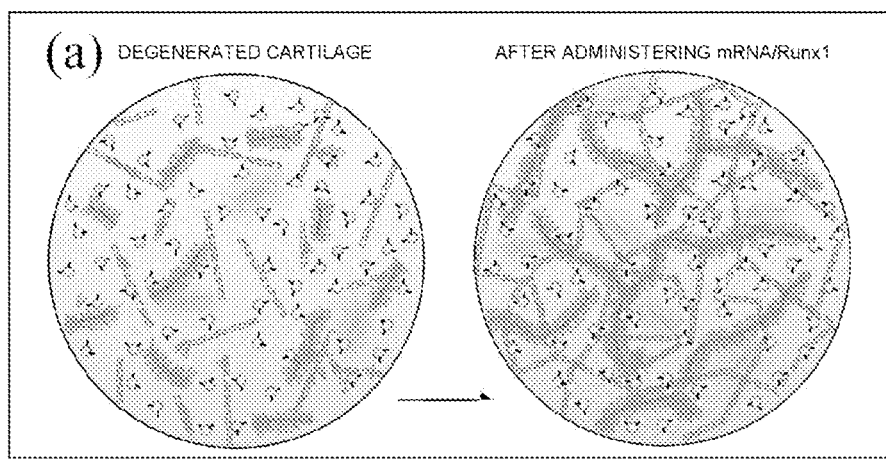
FIG. 8a is diagram showing schematically a resynthesis of glycosaminoglycan by administering mRNA subjected to Runx1 encoding, to an affected cartilage.
FIG. 8b is a diagram showing schematically a variation in a spectrum of a degenerated cartilage and a cartilage regenerated by administering mRNA/Runx1.
Figure 8:
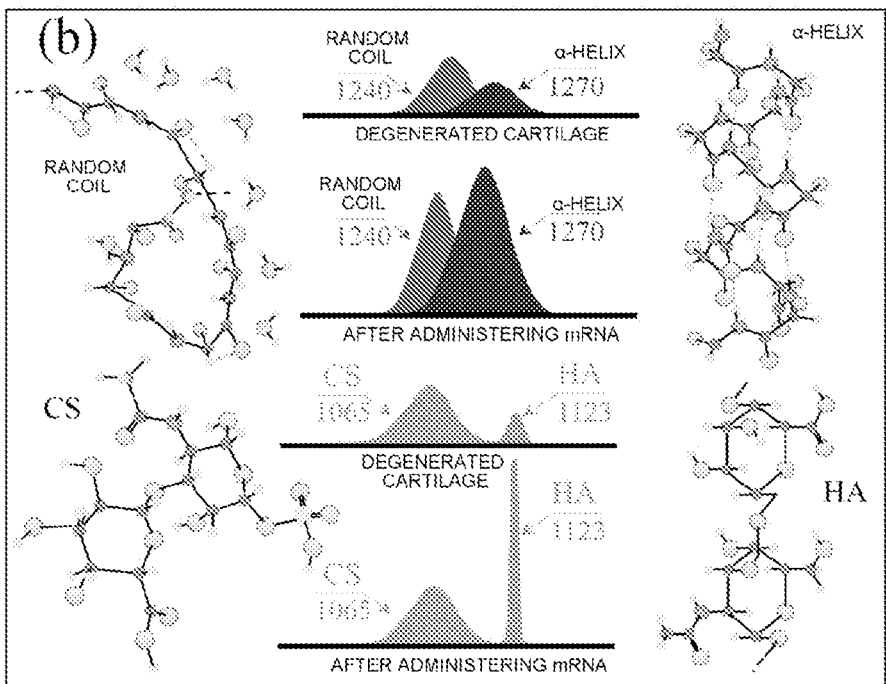

A relationship of time after the OA surgery and a Raman spectral ratio in a glycosaminoglycan region is shown in FIG. 7 (FIG. 7a, FIG. 7b, and FIG. 7c). FIG. 7a shows a relationship of time after the OA surgery and a spectral intensity ratio ($I_{1065}/I_{1123}$) representing a content ratio of chondroitin sulfate and hyaluronic acid in a cartilage. FIG. 7b shows a relationship of time after the OA surgery and a spectral intensity ratio ($I_{1165}/I_{850}$) representing a level of glycosylation of protein in a cartilage. Moreover, in FIG. 7a and FIG. 7b, a hatched portion in a graph shows each spectral intensity ratio one week after administering mRNA/Runx1.

A value of $I_{1065}/I_{1123}$ decreased substantially two weeks after the OA surgery, and increased thereafter (FIG. 7a). Whereas. $I_{1165}/I_{850}$ increased two weeks after the OA surgery and decreased thereafter (FIG. 7b). This indicates that in the degeneration of cartilage, a change in the composition of glycosaminoglycan occurs in two stages.

FIG. 7c is a diagram showing schematically a change in glycosaminoglycan in the degeneration of cartilage. In a first stage, due to the loosening of the collagen secondary structure mentioned above, HA included abundantly in a joint fluid is susceptible to move inside the cartilage, and moreover, HA, being highly hydrophilic, is accumulated inside the cartilage structure having an increased hydration level. Furthermore, in response to an extracellular matrix degeneration, hyaluronic acid synthesis from the chondrocytes is accelerated, and as a result, the content ratio CS/HA decreases (accumulation—biosynthesis stage, up to about two weeks after the OA surgery). Next, as the degeneration of cartilage progresses further in the second stage, due to the degradation of GAG and the decrease in the GAG secretion from the chondrocytes, while the content ratio of CS/HA returns to a value before the OA surgery, the band intensity of the overall GAG region decreases (degradation stage). The accumulation—biosynthesis stage is a reversible reaction, and it is presumed that when it comes to the degradation stage, the irreversible state is assumed gradually.

Moreover, in FIG. 7a and FIG. 7b, each spectral ratio one week after administering mRNA/Runx1 was restored to a value close to that for the normal cartilage. Thus, it was confirmed that predefined spectral ratios representing the composition of glycosaminoglycan and the level of glycosylation reflected the fact that the cartilage-inducing ability of chondrocytes was activated by the therapeutic medication, which resulted in an increase in the secretion of glycosaminoglycan (hyaluronic acid in particular) and the accumulation and rearrangement within the cartilage matrix.

Regarding the change in the amide region and the glycosaminoglycan region observed, one of the conceivable prime causes of the change is a local rise in temperature due to friction at a cartilage surface caused due to the joint instability. It has been known that a structural change of protein is induced due to a temperature change, and it is presumed to have become a cause of inducing the change in the collagen secondary structure observed in the amide region. Moreover, it is presumed that the change in the glycosaminoglycan region is induced due to an increase in the transfer of hyaluronic acid into the cartilage matrix and an effect on the chondrocytes. Usefulness of Raman spectroscopy was demonstrated as a method for directly detecting these molecular-level changes in a physiological tissue.

In the abovementioned examples, for samples in the initial stage of cartilage degeneration up to four weeks after the OA surgery, Raman spectrometry was performed, and indices which determine the degree of degeneration were found out. On the other hand, for the normal cartilage and cartilage two weeks after and four weeks after the OA surgery, when X-ray photography and histological observation were carried out and the comparison was made, no difference was observed, and progression of the cartilage degeneration could not be identified. Thus, by using Raman spectroscopy, and calculating the values representing specified indices, it was demonstrated that it is possible to determine the degree of degeneration of cartilage in the initial stage as compared to that by a conventional method. Furthermore, it was demonstrated that by activation of the cartilage-inducing ability of chondrocytes by administering mRNA/Runx1, it is possible to determine the drug action which restores and improves this change.

Although the present invention was described heretofore by referring to the embodiments and examples, the present invention is not limited to the embodiments and examples described heretofore. Various modifications within the scope of the claimed invention that can be understood by a person skilled in the art can be made in structures and details of the claimed invention.

The present application is based upon and claims the benefit of priority from Japanese Patent Application No. 2021-018138 filed on Feb. 8, 2021, the entire contents of which are incorporated herein by reference.

The invention claimed is:

1. A cartilage degeneration analyzer comprising:
a processor which includes an index calculator configured to calculate, based on a Raman spectrum obtained by Raman spectrometry in which excitation light is irradiated to cartilage of a subject, a value representing at least one index from a group consisting of
Index (a):
hydration level of collagen,
Index (b): composition and total amount of glycosaminoglycan, wherein the composition of glycosaminoglycan is a quantitative ratio of chondroitin sulfate and hyaluronic acid, and
Index (c): level of glycosylation of protein and total amount of glycosaminoglycan.

2. The analyzer according to claim 1, wherein the processor further includes a judging section which is configured to determine a degree of cartilage degeneration based on the value calculated by the index calculator.

3. The analyzer according to claim 1, wherein Index (a) is calculated based on a Raman spectrum in a region of wavenumbers from 1170 cm$^{-1}$ to 1500 cm$^{-1}$.

4. The analyzer according to claim 1, wherein Index (b) and Index (c) are calculated based on a Raman spectrum in a region of wavenumbers from 1000 cm$^{-1}$ to 1200 cm$^{-1}$.

5. The analyzer according to claim 1, wherein the value representing Index (a) is a ratio (($I_{1312}+I_{1340}/I_{1270}$) of a sum of an integrated intensity ($I_{1312}$) of a peak of a range from 1307 cm$^{-1}$ to 1317 cm$^{-1}$ and an integrated intensity ($I_{1340}$) of a peak of a range from 1335 cm$^{-1}$ to 1345 cm$^{-1}$, and an integrated intensity ($I_{1270}$) of a peak of a range from 1265 cm$^{-1}$ to 1275 cm$^{-1}$.

6. The analyzer according to claim 1, wherein in Index (b),
the value representing the composition of glycosaminoglycan is a ratio ($I_{1065}/I_{1123}$) of an integrated intensity ($I_{1065}$) of a peak of a range from 1060 cm$^{-1}$ to 1070 cm$^{-1}$ and an integrated intensity ($I_{1123}$) of a peak of a range from 1118 cm$^{-1}$ to 1128 cm$^{-1}$, and
the value representing the total amount of glycosaminoglycan is a sum total of integrated intensities intensity of the peaks of the range of wavenumbers from 1000 cm$^{-1}$ to 1200 cm$^{-1}$.

7. The analyzer according to claim 1, wherein in Index (c), the value representing the level of glycosylation of protein is a ratio ($I_{1165}/I_{850}$) of an integrated intensity ($I_{1165}$) of a peak of a range from 1160 cm$^{-1}$ to 1170 cm$^{-1}$ and an integrated intensity ($I_{850}$) of a peak of a range from 845 cm$^{-1}$ to 855 cm$^{-1}$, and the value representing the total amount of glycosamino-glycan is a sum total of integrated intensities intensity of the peaks of the range of wavenumbers from 1000 $cm^{-1}$ to 1200 $cm^{-1}$.

8. The analyzer according to claim 1, wherein the analyzer is used for diagnosis of osteoarthritis.

9. A method for determining a degree of cartilage degeneration comprising:

calculating, based on a Raman spectrum obtained by Raman spectrometry in which excitation light is irradiated to cartilage of a subject, a value representing at least one index from a group consisting of Index (a):

hydration level of collagen,

Index (b): composition and total amount of glycosami-noglycan, wherein the composition of glycosamino-glycan is a quantitative ratio of chondroitin sulfate and hyaluronic acid, and Index (c): level of glycosylation of protein and total amount of glycosaminoglycan; and determining the degree of cartilage degeneration based on the value calculated.

10. A method for evaluating a drug action of a test substance, comprising:

calculating, based on a Raman spectrum from cartilage obtained by irradiating a part of cartilage of a subject administered with the test substance with excitation light, a value representing at least one index from a group consisting of Index (a):

hydration level of collagen,

Index (b): composition and total amount of glycosami-noglycan, wherein the composition of glycosamino-glycan is a quantitative ratio of chondroitin sulfate and hyaluronic acid, and Index (c): level of glycosylation of protein and total amount of glycosaminoglycan; and evaluating the drug action of the test substance based on the value calculated.

* * * * *